US011849763B2

(12) United States Patent
Anton

(10) Patent No.: US 11,849,763 B2
(45) **Date of Patent: *Dec. 26, 2023**

(54) BATTERY MODULE FOR ELECTRONIC INHALATION DEVICE

(71) Applicant: Mark Anton, Flanders, NJ (US)

(72) Inventor: Mark Anton, Flanders, NJ (US)

( * ) Notice: Subject to any disclaimer, the term of this patent is extended or adjusted under 35 U.S.C. 154(b) by 107 days.

This patent is subject to a terminal disclaimer.

(21) Appl. No.: 17/315,845

(22) Filed: May 10, 2021

(65) Prior Publication Data

US 2021/0274840 A1 Sep. 9, 2021

Related U.S. Application Data

(63) Continuation-in-part of application No. 15/430,029, filed on Feb. 10, 2017, now Pat. No. 11,000,070.

(Continued)

(51) Int. Cl.

| | |
|---|---|
| ***A24F 40/40*** | (2020.01) |
| ***H01M 10/42*** | (2006.01) |
| ***A24F 40/10*** | (2020.01) |
| ***H02J 7/00*** | (2006.01) |
| ***A24F 40/95*** | (2020.01) |
| ***G06F 1/16*** | (2006.01) |

(52) U.S. Cl.

CPC .............. *A24F 40/40* (2020.01); *A24F 40/10* (2020.01); *A24F 40/95* (2020.01); *H01M 10/425* (2013.01); *H02J 7/0044* (2013.01); *G06F 1/165* (2013.01)

(58) Field of Classification Search

CPC ........ A24F 47/008; A24F 40/10; A24F 40/40; A24F 40/53; A24F 40/60; A24F 40/65; A24F 40/95; A61M 11/042; A61M 2205/3317; A61M 2205/50; A61M 15/06; A61M 2205/3368; A61M 2205/3653; A61M 2205/502; A61M 2205/8206; H04W 88/02; H05B 1/0244; H05B 2203/021; H05B 1/0227; G06F 1/165; H01M 10/425; H01M 2220/30; H02J 7/00032; H02J 7/0044; H02J 7/0045; H02J 7/0047; H02J 7/0063; Y02E 60/10

USPC ................................ 392/386, 390, 391, 404

See application file for complete search history.

(56) References Cited

U.S. PATENT DOCUMENTS

2015/0257447 A1* 9/2015 Sullivan ................ A61M 15/06 131/329

2015/0359263 A1* 12/2015 Bellinger ............. H05B 1/0244 392/394

2016/0183596 A1* 6/2016 Rado ....................... F22B 1/284 392/404

* cited by examiner

*Primary Examiner* — Dana Ross

*Assistant Examiner* — James F Sims, III

(74) *Attorney, Agent, or Firm* — Gearhart Law, LLC

(57) ABSTRACT

The present disclosure relates to battery modules for electronic inhalation devices, namely electronic cigarettes and other vaping devices with superior performance and user control over device variables. In some instances, the present device is configured to properly interpret the attached atomizer's electrical resistance and subsequently calibrate the proper electrical output. This prevents the device from overheating the coil and producing temperatures that will degrade the expected liquids. Further, the user may be able to input a code for the corresponding "flash points" of the intended liquid to determine the optimum output for both delivery of compounds formulated and for the proper temperature range of the device. In other embodiments, the device is configured to interface with an electronic device such as a smart phone.

8 Claims, 6 Drawing Sheets

100 101 102 103 104 105 106 107 108 109 110 111 112 113 117 118

Related U.S. Application Data

(60) Provisional application No. 62/294,715, filed on Feb. 12, 2016.

BATTERY MODULE FOR ELECTRONIC INHALATION DEVICE

CLAIM OF PRIORITY

This application claims priority to U.S. application Ser. No. 15/430,029, filed on Feb. 10, 2017 which claims priority to U.S. Application No. 62/294,715 filed on Feb. 12, 2016, the contents of all of which are fully incorporated herein by reference in its entirety.

FIELD OF THE EMBODIMENTS

The field of the embodiments of the present invention relate to battery modules for electronic inhalation devices, namely electronic cigarettes and other vaping devices with superior performance and increased automated control over device variables.

BACKGROUND OF THE EMBODIMENTS

Vaping devices, such as electronic cigarettes or "e-cigs," allow a user to breathe a vaporized or atomized glycerin or propylene glycol-based solution containing nicotine and/or flavorings and/or other compounds. Electronic cigarettes have existed for some time, but it was not until the turn of the century that the modern e-cig was brought to the masses. These devices produce a smokeless vapor of the liquid solution using an "atomizer" or heating element contained in fluid connection with a liquid reservoir.

The proliferation of such devices has brought about many variations upon the basic model, including those that may be readily modified in some capacity by the user. For example, some e-cigs are capable of communicating with electronic devices and running programs via those devices to influence the activity of the e-cig. Yet other e-cigs allow for the creation of profiles for individual users depending on their personal preferences. Even further, some vaping devices are now built using a variety of parts by a user to create a completely custom vaping experience.

However, these abilities readily cause several unintended consequences by users. For example, as noted, many individuals prefer to mix and match components to create a custom vaping experience. The mixing and matching of parts requires intimate knowledge of how the parts interact with one another to create a functional e-cig. Many times individuals will choose parts that are not compatible and can cause the resulting e-cig to be non-functional or cause damage to the components or even harm to the user.

Further, there is no e-cig or other type of electronic vaping device that can wholly prevent burning or degradation of the liquid used in the vaping process. It is paramount that the resistance of the atomizer or electronic inhalation device is understood such that the voltage and wattage of the device may be calibrated to perfection. Failure to do so may cause dangerous aldehyde containing compounds to be formed and otherwise cause degradation of the liquid bringing about a sub-par vaping experience and potential harm to the user.

Thus, there is a need for an electronic inhalation device that takes into account these needs and prevents the formation of aldehydes and further prevents improper voltages and wattages from being used for a particular atomizer or liquid. This serves to create a constant and consistent flavor profile and preserve battery life of the device. The present invention and its embodiments meets and exceeds these objectives.

REVIEW OF RELATED TECHNOLOGY

U.S. Patent Application 2015/0075546 pertains to an add-on module for an electronic cigarette or vaporizer that provides an electronic means to communicate with remote computers and electronic devices and to provide a dynamic means to control temperature over time, manage and save device settings, dynamically control temperatures, monitor sensors, and transmit and read this data from remote computing devices for display, alteration, and storage.

U.S. Patent Application 2014/0123990 pertains to a real time variable voltage programmable electronic cigarette device that has a main body, a controller, a memory, a visual indicator, a multidirectional joystick for operating and programming the electronic cigarette, a visual indicator for real-time status feedback, and a USB connector for computer connectivity. Programming the device includes the ability to create vaping profiles. The programmable function enables a user to set the voltage output and power output level applied to the atomizer when energized.

Various systems and methodologies are known in the art. However, their structure and means of operation are substantially different from the present disclosure. The other inventions fail to solve all the problems taught by the present disclosure. At least one embodiment of this invention is presented in the drawings below and will be described in more detail herein.

SUMMARY OF THE EMBODIMENTS

In general, the present invention and its embodiments provide a battery for an electronic inhalation device such as an electronic cigarette, atomizer, and/or other vaping device that provides a user with superior performance and automated control over device variables thereby removing the "guesswork" from operating the device.

In some embodiments, the present invention comprises a battery module that is operably coupled to an existing electronic inhalation device. In other embodiments, the present invention is a "pen" type electronic inhalation device with the battery module wholly integrated with the electronic inhalation device. Other embodiments not explicitly named herein may also exist under the purview of this invention.

In one embodiment, the battery module is configured to properly interpret the attached atomizer's electrical resistance and subsequently calibrate the proper electrical output. This prevents the electronic inhalation device from overheating the coil contained within the atomizer and producing temperatures that will degrade the liquid(s) used for vaping. Further, in other embodiments, the user may be able to input a code for the corresponding "flash points" and/or boiling points of the intended liquid to determine the optimum output for both delivery of compounds formulated and for the proper temperature range of the device.

In yet other embodiments, the device is configured to interface with an electronic device such as a smart phone. This may, for example, enable the electronic inhalation device to be paired with a dedicated app or program to monitor variables attributable to the electronic inhalation device, modifying variables attributable to the electronic inhalation device, or the like or some combination thereof.

In one embodiment of the present invention there is a battery module for an electronic inhalation device, the battery module comprising: an adapter configured to couple to the electronic inhalation device; a processor; a non-transitory computer-readable medium comprising machine readable instructions, which when executed by the processor, cause the processor to perform a method, the method comprising the steps of, monitoring at least one electrical property of the electronic inhalation device, and adjusting an electronic output of the battery module based on the at least one electrical property of the electronic inhalation device; and a cell.

In another embodiment of the present invention there is an electronic inhalation system comprising: a battery module for an electronic inhalation device, the battery module comprising, a threaded adapter configured to couple to an atomizer of the electronic inhalation device; a processor; a non-transitory computer-readable medium comprising computer readable instructions, which when executed by the processor, cause the processor to perform a method, the method comprising the steps of, monitoring an electrical resistance of metallic coil of the atomizer, and adjusting an electronic output of the electronic inhalation device based on the electrical resistance of the metallic coil; a cell; and wherein the electronic inhalation device is configured to couple to the battery module.

In yet another embodiment of the present invention there is an electronic inhalation system comprising: an atomizer having at least one metallic coil; a cartridge configured to house a liquid; a battery module comprising, a processor, a non-transitory computer-readable medium comprising computer readable instructions, which when executed by the processor, cause the processor to perform a method, the method comprising the steps of, monitoring an electrical resistance of the at least one metallic coil of the atomizer, and adjusting an electronic output of the electronic inhalation device based on the electrical resistance of the at least one metallic coil, wherein the electronic output is at least one of a wattage or a voltage; and a cell.

In yet another embodiment of the present invention there is a battery for an electronic inhalation device, the battery comprising: a positive terminal and a negative terminal; a port coupled to at least one of the positive and the negative terminal, wherein the port is configured to receive an atomizer of the electronic inhalation device, a processor; and a non-transitory computer-readable medium comprising machine-readable instructions, which when executed by the processor, cause the processor to perform the steps of, determining a composition of a metallic coil of the atomizer, detecting a resistance of the metallic coil of the atomizer, and adjusting an operational mode of the battery based on at least one of the composition and the resistance of the metallic coil.

In still another embodiment of the present invention there is a battery module for an electronic inhalation device having a metallic coil, the battery module comprising: a housing having a top, a bottom, at least one sidewall, and a display; a positive terminal and a negative terminal; a port coupled to at least one of the positive and the negative terminal, wherein the port is configured to receive an atomizer of the electronic inhalation device; a processor; and a non-transitory computer-readable medium comprising machine-readable instructions, which when executed by the processor, cause the processor to perform the steps of, determining a composition of the metallic coil of the atomizer, detecting a resistance of the metallic coil of the atomizer, and adjusting an operational mode of the battery module based on at least one of the composition and the resistance of the metallic coil.

In general, the present invention succeeds in conferring the following, and others not mentioned, benefits and objectives.

It is an object of the present invention to provide a battery module that automatically interprets the electrical resistance of a metallic coil of an atomizer.

It is an object of the present invention to provide a battery module that prevents over heating of the coil, thereby preventing degradation of the e-liquid.

It is an object of the present invention to provide a battery module that allows for user modification of the settings of the device.

It is an object of the present invention to provide a battery module that is configured to interface with an electronic device.

It is an object of the present invention to provide a battery module that tallies or counts the number of "puffs" a user takes of the device.

It is an object of the present invention to provide a battery module that automatically determines the proper operating temperature, variable wattage, and other parameters for the device.

DESCRIPTION OF THE PREFERRED EMBODIMENTS

Figure 1:
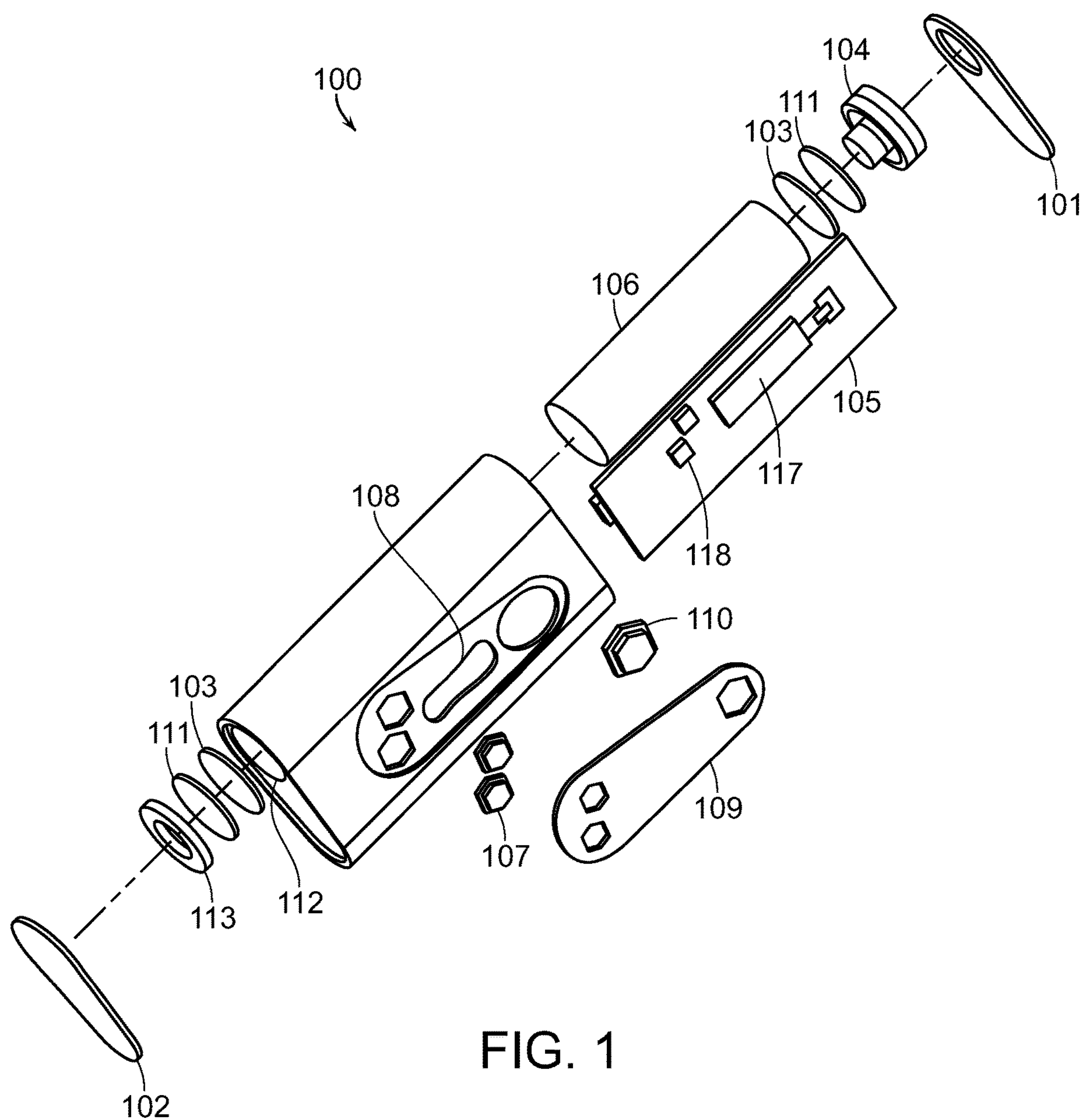
FIG. 1 is an exploded view of at least some of the components of an embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Referring now to FIG. 1, there is an embodiment of the present invention in an exploded view illustrating at least some of the components of the embodiment. The battery module 100, as shown, contains at least a top cover 101, threading 104, insulators 111, cell 106, depressible buttons 107, activation button 110, display 108, bottom cover 102, cell holder 113, cell housing 112, printed circuit board (PCB) 105, processor 117, memory 118, EVA 103, display cover 109 or some combination thereof.

The battery module 100 may be capable of being threadably engaged via threads 104 (or otherwise coupled) to retrofit to an electronic inhalation device 120 (see FIG. 2), such as an electronic cigarette or atomizer or tank or the like. In other embodiments, the battery module 100 is fully integrated into the electronic inhalation device thereby forming a single unit device (see FIG. 4).

When coupled to an electronic inhalation device 120, an operable electronic connection is established between the battery module 100 and the electronic inhalation device 120. Upon establishing this connection, the battery module 100 is configured to automatically detect the resistance of the wire coil contained within the atomizer, or similar structure, of the electronic inhalation device 120. Further, the composition of the metallic coil(s) may be ascertained (e.g., nickel, Kanthal, stainless steel, etc.). The composition of the metallic coil is based off electronic "pings" generated by the device to calculate the variance in the results to determine the types of metals in the atomizer.

Once the resistance and/or composition has been determined, the battery module 100 can determine which mode it would be preferential to operate: 1) resistance mode—where wattage or voltage is fixed or 2) temperature mode—where the temperature is automatically calculated and set. In yet another embodiment, the temperature mode may allow for the components of the battery module 100 to be configured to calculate air flow and subsequent determination of dose provided by the aerosol. This is accomplished via a calculation of current of the metallic coil to attain a certain temperature of the metallic coil as air flow plus liquid (to be vaporized) cool the coil, and the corresponding decrease in temperature is then calculated. This then becomes a factor of power and the increased power needed to compensate for the reduction in temperature can be reasonably ascertained by the coefficient of gas cooling and the coefficient of cooling a liquid.

Figure 5:
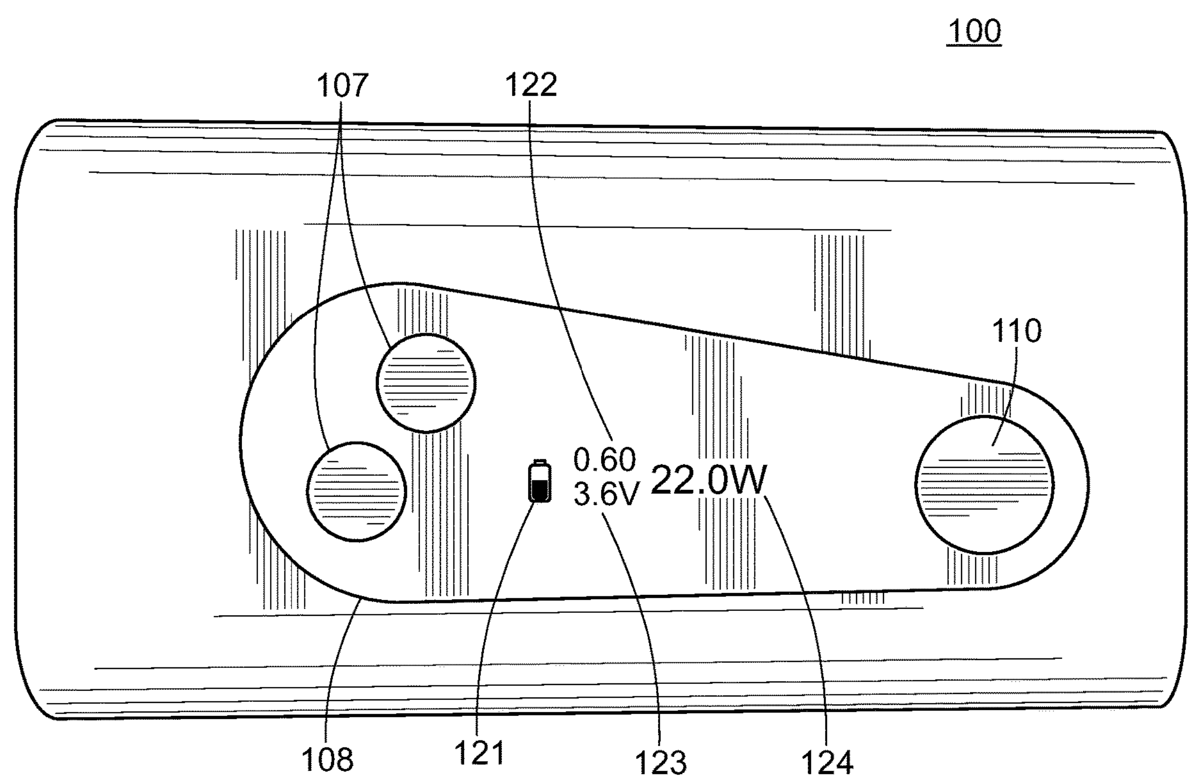
FIG. 5 is a front view of a display of an embodiment of the present invention.
Figure 6:
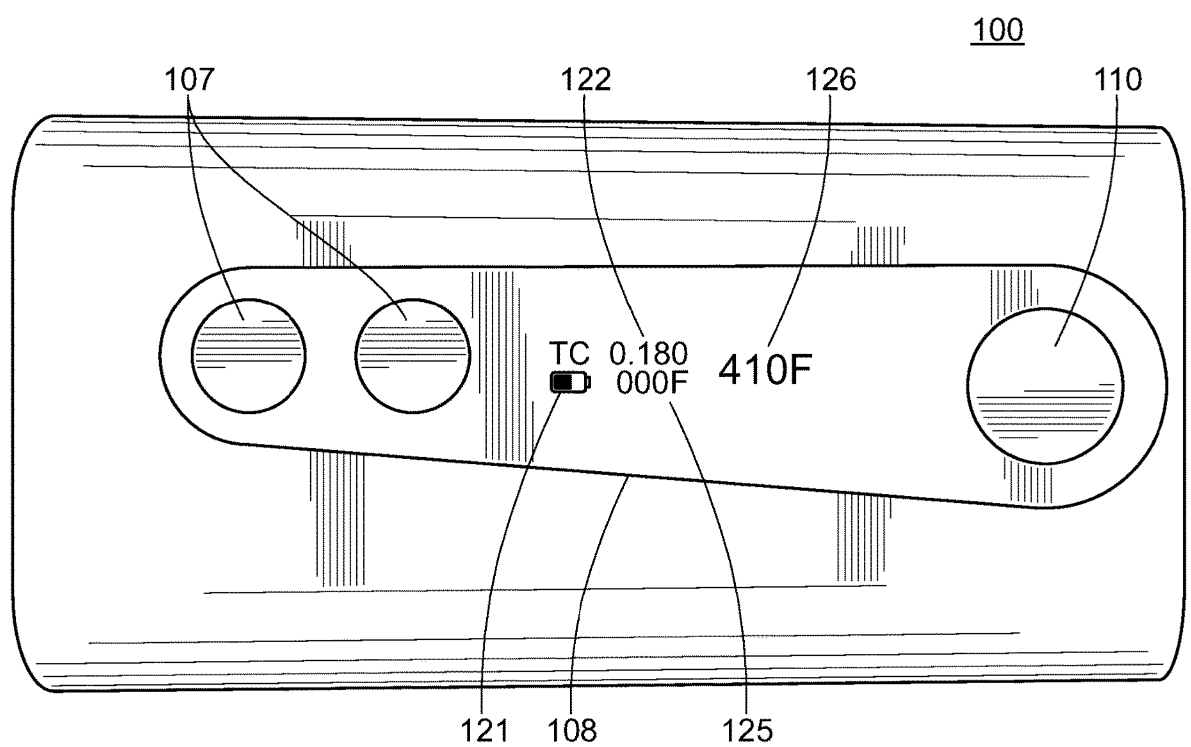
FIG. 6 is a front view of an alternate display of an embodiment of the present invention.

The resistance mode device is shown in FIG. 5 and the temperature mode device is shown in FIG. 6, however, each battery module 100 may be capable of operating on only one or in both modes as described herein.

The resistance detection may be achieved in several fashions and may operate similar to an ohmmeter including but not limited to the sending of a first electric pulse or a first constant current or first constant voltage or a combination thereof.

Such a pulse or current will allow calculations to be performed via the processor 117, to determine the resistance of the coil in the atomizer. A "test puff" may be required to allow the requisite data to be gathered and the necessary calculations to be completed. In addition, this realization of the resistance may further occur in real time as the connection is made between the battery module 100 and the electronic inhalation device 120.

By enabling the calculations to be completed as described above, both (or either) of a wattage and a voltage may be calculated for which the electronic inhalation device 120 will operate as limited by the battery module 100. These specific values may be dependent on the resistance in the atomizer and will allow for autonomous and automatic setting of the battery module variables.

In addition, the processor 117 and memory 118 may be programmed and have stored thereon information (machine readable instructions) that acts as safety measures for operation of the battery module 100. For example, the battery module 100 may be able to prevent firing or activation if no liquid or an inadequate amount of liquid is present in the reservoir of the electronic inhalation device 120. In other embodiments, to prevent overheating or inadvertent activation, the battery module 100 automatically deactivates after about ten (10) seconds of continuous use. In other embodiments the time for deactivation to occur may vary and may be configurable by the user.

Further, the functional wattage and voltage can be optimized for the specific atomizer or electronic inhalation device 120 being employed by the user. This, is turn, prevents overheating of the coil(s) of the atomizer or electronic inhalation device 120. By preventing the coil(s) of the atomizer from overheating, the operational temperatures of the electronic inhalation device will be such that degradation of the vaping liquid will be eliminated or diminished. Overheating of the vaping liquid can create an acrid taste for the user as well as lead to the formation of aldehyde containing compounds which are highly dangerous for the user.

Figure 2:
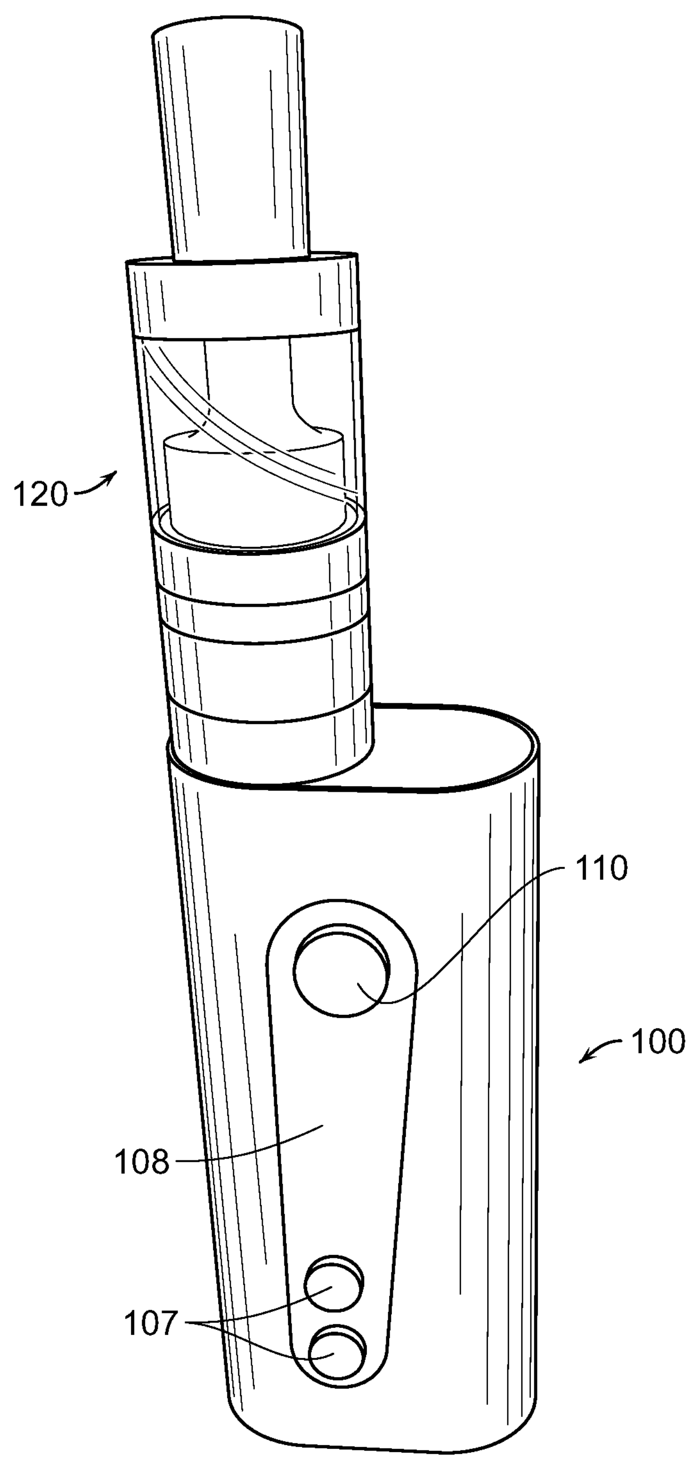
FIG. 2 is a perspective view of an embodiment of the present invention.
Figure 3:
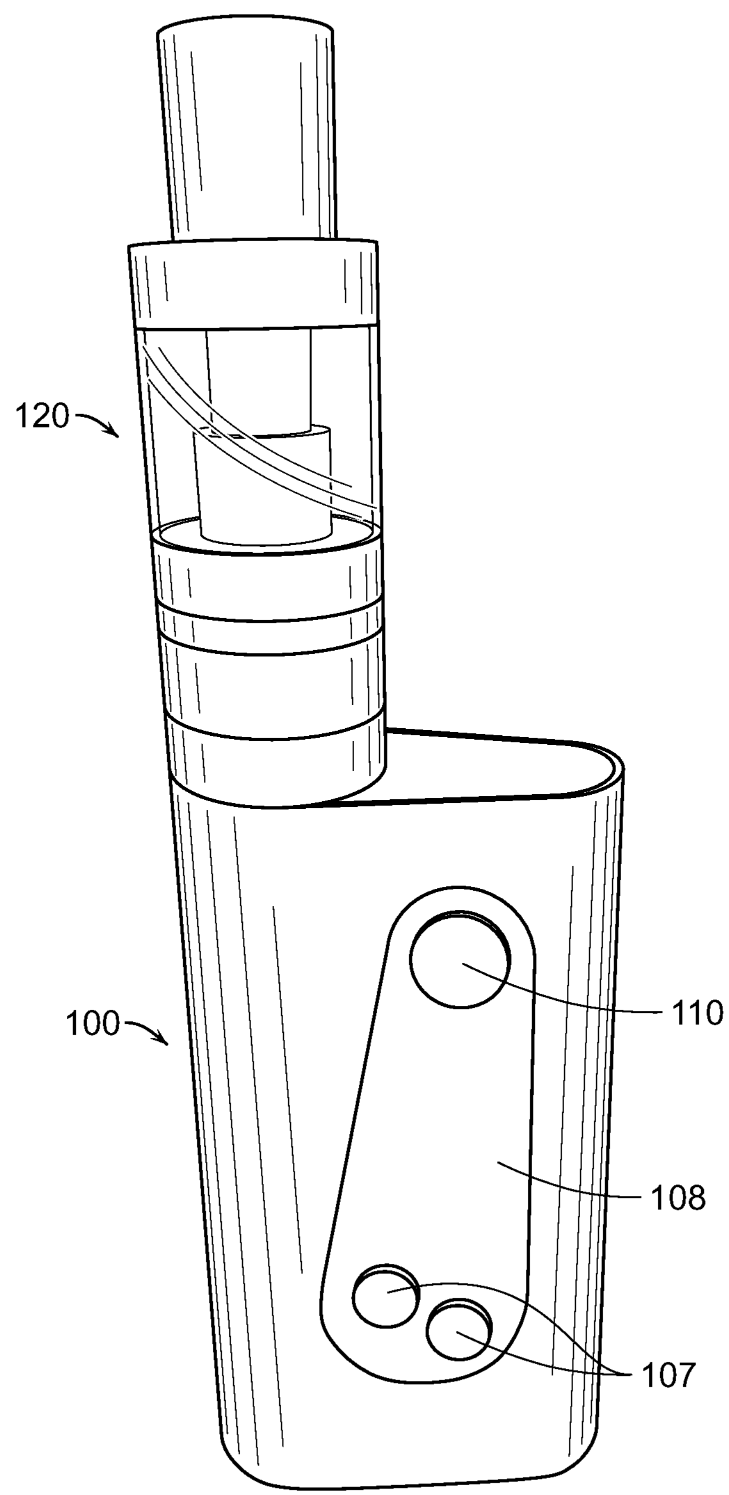
FIG. 3 is a perspective view of a second embodiment of the present invention.
Figure 4:
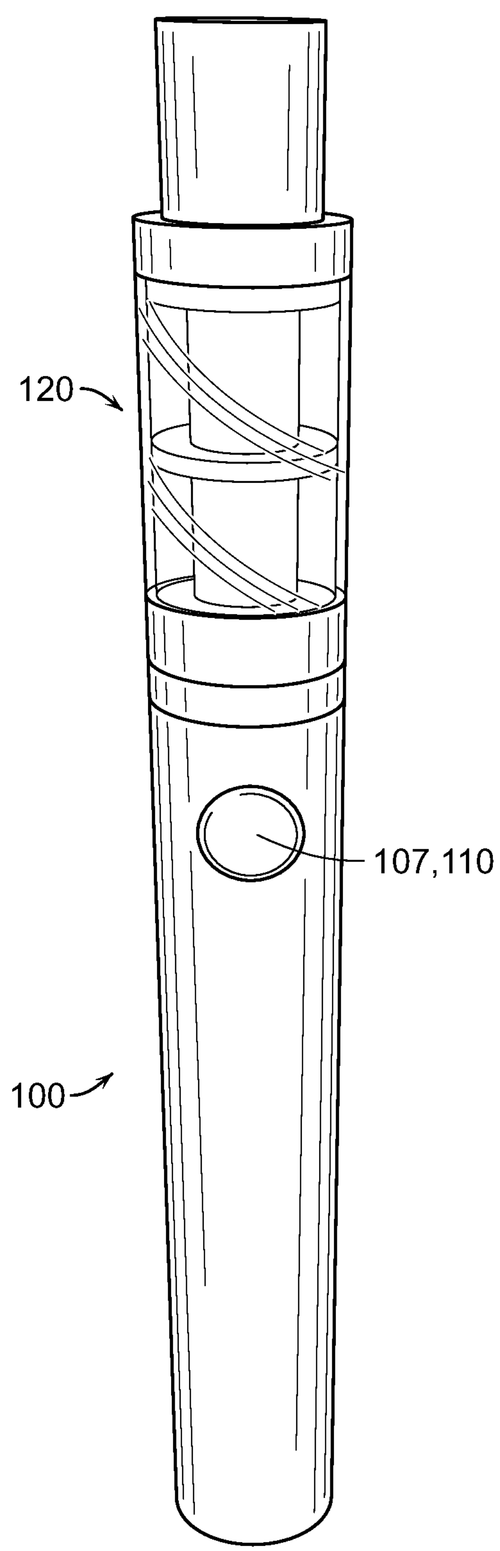
FIG. 4 is a perspective view of a third embodiment of the present invention.

FIGS. 2-4 demonstrate varying embodiments of the present invention. The embodiments shown in FIGS. 2 and 3 are similar in respect to have a battery module 100 that is coupled to an electronic inhalation device 120. The embodiment shown in FIG. 4 is integrated into a "pen" device thereby removing the need for the bulky battery module 100.

Referring now to FIGS. 2 and 3 each of the battery modules 100 is shown with function buttons 107, an activation button 110, and a display 108. When the battery module 100 is coupled to the electronic inhalation device 120, the display 108 is configured to communicate to a user information specific to the setup of the device (see FIGS. 4-5). Such information may include the operating temperature, wattage, resistance, and the like. Each of the embodiments may be capable of automatically detecting, without user input, the parameters of the electronic inhalation device 120 for proper usage, optimal flavor, and prolonged battery life.

In FIG. 4, the button functions as both a function button 107 and an activation button 109. Further, the battery module 100 is in a "pen"-like structure allowing the combination of the battery module 100 and electronic inhalation device 120 to form a more traditionally shaped e-cigarette type device.

In some embodiments, this not only allows for resistance control, as noted herein, by the battery module 100 but further allows for temperature control via the function button 107. In some embodiments, depressing the function button 107 three times causes the device to change between predetermined temperatures for usage. In other embodiments, holding and depressing the function button 107 causes it to serve as an activation button 109 which causes the device to activate and allows vapor to be drawn by the user. In some embodiments, a light source is used to alert the user to the settings of the device. In other embodiments, a display is included to communicate this information to the user.

Referring now to FIGS. 5 and 6, there are displays associated with embodiments of the present invention. In FIG. 5, the display 108 has a battery display 121, voltage display 123, resistance display 122, wattage display 124 visible. In some embodiments, the display 108 may have more or fewer variables visible at one time. In other embodiments, the manner of display (i.e., variables which are displayed) may change and such a change may be initiated by the user to customize their experience. The display 108, as shown, is flanked by function buttons 107 and activation button 109. In FIG. 6, the display 108 features a battery display 121, resistance display 122, temperature display 126, and temperature readout 126. Again, the display 108 is flanked by function buttons 107 and activation button 109. Further, the display 108, as shown, may have the same potential modifications as described above.

FIG. 5 illustrates a battery module 100 intended to allow a user to modify the voltage and/or the wattage output of the battery module 100. A user preferably couples the electronic inhalation device to the battery module 100 and the resistance of the coil in the electronic inhalation device (atomizer) is read automatically. In some instances, a nickel wire may be employed by the electronic inhalation device, and in other instances a resistive-type wire may be employed. Once the resistance is read, the voltage and wattage can be automatically set to optimize the flavor profiles, minimize harmful byproducts, and preserve battery life, amongst other desirables.

In addition, a user may use the function buttons 107 to cause the voltage and or wattage to increase or decrease to further suit their needs. Further, a use may use a particular combination of buttons including the activation button 109 to switch between varying modifiers to be shown on the display. In some embodiments, this may include depressing multiple buttons at once or in other embodiments using a single button depressed in succession. For example, in FIG. 5, to switch from the wattage output being modified to the voltage output, a user may depress the activation button 109 three times in succession. After which, the user may use the function buttons 107 to increase or decrease the voltage of the device.

In another embodiment, holding a function button 107 and the activation button 109 may cause the display 108 to change to a "puff counting display" which counts the number of puffs or hits taken by a user during usage of the device. This change in display may remain active on the display or may only show for a predetermined amount of time before reverting to a display similar to that shown in FIG. 5. Other functions and information not explicitly stated herein may also be shown by the display.

Referring now to FIG. 6, the display 108 features at least a resistance display 122, temperature display 126, and temperature readout 126. The resistance is automatically calculated by the device which then, in this embodiment, causes the temperature to be automatically configured to maximize flavor profiles, prevent formation of harmful byproducts, and preserve battery life, amongst other desirable features. The temperature readout 125 may adjust when the activation button 109 is held showing the temperature of the coil as it heats and then causing it to remain steady while the activation button is held. The user can further manipulate the temperature using the function buttons 107. The device 100 automatically determines the set up between temperature mode or wattage mode by detecting the resistance and variation of makeup of the coil.

The battery display 121 shows a relative level of "life" left in the battery or other cell of the battery module 100. In some embodiments, this is shown graphically whereas in other it forms a percentage or other visual readout capable of being interpreted. The cell may be rechargeable via conventional recharging means such as a USB port or may require changing of the cell once depleted.

The battery module 100 described in FIGS. 1-6 has been generally described and other iterations may be employed combining some or all the elements described herein. In some instances, other uses are envisioned for the battery module 100.

In some embodiments, the battery module 100 further comprises a digital gyroscope contained therein. Not only does this allow for the device to "understand" it orientation, but it can also be used to track the movements corresponding to the device being brought to a user's lips and if the device is indeed used to vape each time the device is brought to the lips indicating usage patterns for the user. Further, the gyroscope may prevent in inadvertent activation of the device when in an upright position, as shown in the FIGS., as opposed to the "tilted" position when the device would typically be brought to a user's lips for vaping.

In another embodiment, the device interfaces with an electronic device such as a laptop computer, desktop computer, gaming system, smart phone, smart watch, head mounted display, smart television, multimedia player, and the like or some combination thereof. Such a connection may require the battery module 100 to employ a wireless transceiver, such as a Bluetooth® transceiver, to facilitate communication between the remote devices.

Once communicatively paired to the electronic device, the user may be able to control and/or monitor the battery module 100 and any associated electronic inhalation device 120 from the electronic device. Further, the device may be monitored or manipulated by a third party such as a medical professional. In such an implementation, a doctor may monitor the usage and issue various alerts to the user as a part of a smoking cessation program. Other potential uses and embodiments are also envisioned.

Further, the device may be used to atomize or aerosolize other materials outside of the conventional nicotine-based glycol formulations currently abundant in the marketplace. In some embodiments, various pharmaceuticals may be used in conjunction with the device providing an inhalable form of the pharmaceutical whereby absorption and bioavailability will be increased. In one embodiment the "active" ingredient in the liquid is cannabidiol (CBD). In other embodiments, the device may be used with liquids containing other medicants such as antidotes or countermeasures to harmful substances (chemical weapons, biological substances, radiation, etc.) which people may encounter.

In yet other embodiments, a user may use the various inputs, or depressible buttons, of the battery module to enter a code corresponding to a "flash point" of the liquid containing the cartridge of the electronic inhalation device. This enables the parameters of the battery module to be modified such that it corresponds to this flash point thereby preserving the flavor of the liquid as well as preserving battery life of the device.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A battery for an electronic inhalation device, the battery configured to connect to an atomizer of the inhalation device, wherein the battery comprises:

a processor; and a non-transitory computer-readable medium comprising machine-readable instructions, which when executed by the processor, cause the processor to perform the steps of, determining a composition of a metallic coil of the atomizer, detecting a resistance of the metallic coil of the atomizer, and adjusting an operational mode of the battery based on at least one of the composition and the resistance of the metallic coil.

2. The battery of claim 1 wherein adjusting the operational mode of the battery modifies an electrical output of the battery.

3. The battery of claim 1 further comprising a housing and a display coupled to the housing.

4. The battery of claim 3 wherein display is configured to display at least one property of the battery.

5. The battery of claim 4 wherein the at least one property is a level of charge of the battery.

6. A battery module for an electronic inhalation device, the battery module configured to connect to an atomizer of the inhalation device, said atomizer having a metallic coil, wherein the battery module comprises:

a housing having a top, a bottom, at least one sidewall, and a display;

a processor; and a non-transitory computer-readable medium comprising machine-readable instructions, which when executed by the processor, cause the processor to perform the steps of, determining a composition of the metallic coil of the atomizer, detecting a resistance of the metallic coil of the atomizer, and adjusting an operational mode of the battery module based on at least one of the composition and the resistance of the metallic coil.

7. The battery module of claim 6 further comprising at least one depressible button.

8. The battery module of claim 7 wherein the at least one depressible button modifies an output of the battery module.

* * * * *